(12) United States Patent
Zysk et al.

(10) Patent No.: US 11,226,189 B2
(45) Date of Patent: Jan. 18, 2022

(54) METHOD AND APPARATUS FOR CLASSIFYING CORE BIOPSY SPECIMENS WITH OPTICAL COHERENCE TOMOGRAPHY

(71) Applicant: DIAGNOSTIC PHOTONICS, INC., Chicago, IL (US)

(72) Inventors: Adam M. Zysk, Chicago, IL (US); Andrew J. Cittadine, Winnetka, IL (US)

(73) Assignee: DIAGNOSTIC PHOTONICS, INC., Chicago, IL (US)

( * ) Notice: Subject to any disclaimer, the term of this patent is extended or adjusted under 35 U.S.C. 154(b) by 0 days.

(21) Appl. No.: 16/964,045

(22) PCT Filed: Jan. 25, 2019

(86) PCT No.: PCT/US2019/015102
§ 371 (c)(1),
(2) Date: Jul. 22, 2020

(87) PCT Pub. No.: WO2019/147908
PCT Pub. Date: Aug. 1, 2019

(65) Prior Publication Data
US 2021/0003384 A1    Jan. 7, 2021

Related U.S. Application Data

(60) Provisional application No. 62/622,533, filed on Jan. 26, 2018.

(51) Int. Cl.
*G01B 9/02* (2006.01)
*A61B 10/00* (2006.01)
(Continued)

(52) U.S. Cl.
CPC ...... *G01B 9/02091* (2013.01); *A61B 10/0096* (2013.01); *A61B 10/0233* (2013.01); *G01N 21/45* (2013.01); *G01N 33/4833* (2013.01)

(58) Field of Classification Search
CPC ............ G01B 9/02091; A61B 10/0096; A61B 10/0233; G01N 21/45; G01N 33/4833
See application file for complete search history.

(56) References Cited

U.S. PATENT DOCUMENTS

2007/0203404 A1    8/2007    Zysk et al.
2011/0092823 A1    4/2011    Tearney et al.
(Continued)

OTHER PUBLICATIONS

PCT Search Report issued in related application PCT/US2019/015102, dated Jul. 5, 2019, 2 pages.
(Continued)

*Primary Examiner* — Tri T Ton
(74) *Attorney, Agent, or Firm* — Faegre Drinker Biddle & Reath LLP

(57) ABSTRACT

Described herein are an apparatus and method by which at least one core specimen is obtained from a patient. The specimen is optionally placed on a tray, in a holder, or in another device designed to hold the tissue specimen; images of the specimens are acquired with optical coherence tomography, optical coherence tomography image data and, optionally, data from an additional imaging or analysis method, and when analyzed with the tissue classification process yield information on one or more of: the adequacy of the specimens obtained; the likelihood that they contain abnormal or malignant tissue; the regions and/or specimens most likely to contain diagnostic tissue; the approximate dimensions, area, or volume of the abnormal tissue; and the probable type of abnormality.

3 Claims, 11 Drawing Sheets

(51) Int. Cl.
 *A61B 10/02* (2006.01)
 *G01N 21/45* (2006.01)
 *G01N 33/483* (2006.01)

(56) References Cited

U.S. PATENT DOCUMENTS

| | | |
|---|---|---|
| 2014/0031677 A1 | 1/2014 | Iftimia et al. |
| 2014/0212892 A1 | 7/2014 | Gough et al. |
| 2015/0173619 A1 | 6/2015 | Zvuloni et al. |
| 2016/0367228 A1 | 12/2016 | Solomon et al. |
| 2017/0131311 A1* | 5/2017 | Flagle .................. A61B 6/4405 |
| 2019/0313976 A1* | 10/2019 | Hendriks ............. A61B 5/4381 |

OTHER PUBLICATIONS

PCT Written Opinion issued in related application PCT/US2019/015102, dated Jul. 5, 2019, 5 pages.

* cited by examiner

METHOD AND APPARATUS FOR CLASSIFYING CORE BIOPSY SPECIMENS WITH OPTICAL COHERENCE TOMOGRAPHY

CROSS-REFERENCE TO RELATED APPLICATIONS

The present application is the U.S. national phase of the International Patent Application No. PCT/US2019/015102, filed Jan. 25, 2019, which claims the priority benefit of U.S. Provisional Patent Application No. 62/622,533, filed Jan. 26, 2018 and incorporated herein by reference in its entirety.

TECHNICAL FIELD

The present disclosure relates to a method and apparatus for imaging and classifying the tissue type present in core biopsy specimens via the use of optical coherence tomography (OCT) imaging and a tissue identification process.

BACKGROUND

Core needle biopsies, including vacuum-assisted needle biopsies, are taken to acquire solid tissue specimens to aid in the diagnosis and staging of disease. The procedure is often initiated due to an abnormal examination or imaging finding in the breast, prostate, lung, liver, thyroid, kidney, pancreas, and other organs. In the breast, the procedure is typically performed under imaging guidance (magnetic resonance imaging (MRI), ultrasound, or x-ray) to aid in the placement of the needle in the region most likely to contain disease. Multiple tissue specimens, often referred to as "cores" or "core specimens," are often acquired in a single biopsy procedure. Approximately 6-12 cores are usually acquired.

Core specimens can be assessed visually or with an x-ray radiography at the point of care. A laboratory-based histopathology examination is typically performed after the biopsy procedure.

For example, in breast cancer, x-ray radiography of the core specimens is used to locate calcifications (i.e., small calcium deposits that can indicate the presence of malignancy) and to correlate the calcifications with those in a prior mammogram. This x-ray examination of the specimens may assist in assessing the adequacy of the core specimens acquired and identifying core specimens of interest, but is not used to assess malignancy or provide a diagnosis.

Histopathology examination of core specimens is used to make a diagnosis. In this examination, a pathologist uses a light microscope to visualize slides containing stained slices of the core specimens. This examination is conducted after the core needle biopsy procedure. The time between the core biopsy procedure and a pathology report is typically several days. A drawback of histopathology examination is that it is a time-consuming and labor-intensive process that requires assessment of many slides. Additionally, if multiple histopathology tests are required, the quantity of tissue available for testing may be a problem and require a subsequent biopsy to obtain additional tissue.

Several problems exist in this core specimen acquisition and examination process. 1) Approximately 5% of breast core needle biopsy procedures result in the acquisition of inadequate core specimens to make a diagnosis (i.e., they miss the target tissue). 2) Patients must wait several days to learn a diagnosis, yielding significant stress. 3) Pathologists typically examine many slides that contain only healthy tissue, spending valuable time that would be more effectively used to assess the most diagnostically important slides and tissue regions. 4) An insufficient quantity of abnormal tissue available for testing may require an additional biopsy procedure.

Optical coherence tomography is an imaging method that can provide three-dimensional microscopic structural information from tissue specimens. It is frequently used in clinical practice to assess retinal structure and has been used in breast cancer research to assess the margins of excised lumpectomy specimens. Some biopsy needles used by researchers have incorporated optical coherence tomography. These needles seek to provide feedback at the point of tissue acquisition before tissue acquisition.

SUMMARY

Apparatuses and methods in accordance with various embodiments provide a way to image and classify core biopsy specimens after removal, yielding feedback on core biopsy adequacy, core specimen pathology, and the core specimens and/or regions of interest.

Described herein are an apparatus and method by which at least one core specimen is obtained from a patient. The specimen is optionally placed on a tray, in a holder, or in another device designed to hold the tissue specimen. Images of the specimen are acquired with optical coherence tomography and, optionally, other imaging and/or sensing technologies. In an embodiment, such tray, holder, or device will (1) be adapted for OCT imaging of the entirety of each specimen, (2) include an optically transmissive region through which an OCT sample arm beam can pass, (3) position the specimens vertically such that the focus of an OCT sample arm beam is located within the specimens, (4) include a means to maintain specimen orientation during imaging, (5) include a means to prevent dehydration or other alterations of specimen integrity, and (6) include a means to maintain the segregation and labeling of each specimen so that imaging feedback can be given for individual specimens.

Images are analyzed using a tissue classification process. The optical coherence tomography image data and, optionally, data from an additional imaging or analysis method (e.g., x-ray radiography or Raman spectroscopy), when analyzed with the tissue classification process, yield information on one or more of: the adequacy of the specimens obtained; the likelihood that they contain abnormal or malignant tissue; the regions and/or specimens most likely to contain diagnostic tissue; the approximate dimensions, area, or volume of the abnormal tissue; and the probable type of abnormality (e.g., in the breast, abnormal tissue types can include invasive ductal carcinoma, fibroadenoma, ductal carcinoma in situ, lobular carcinoma, and other benign and malignant abnormalities).

DRAWINGS

The foregoing features will be more readily understood by reference to the following detailed description, taken with reference to the accompanying drawings, in which.

Figure 3A:
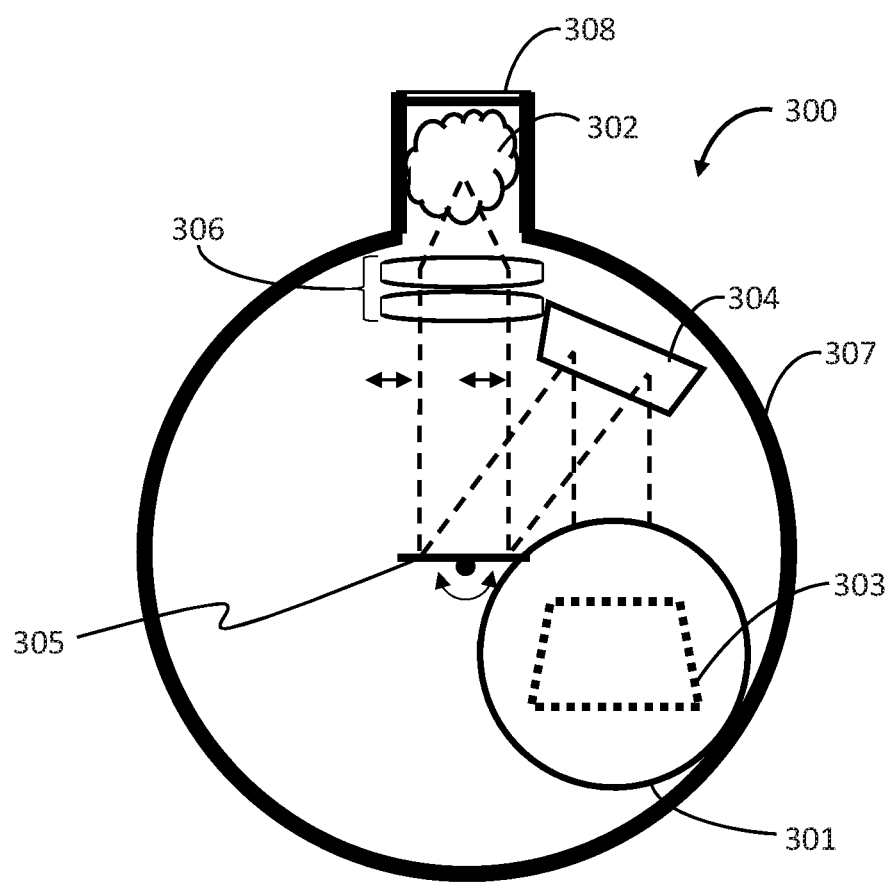
Figure 3B:
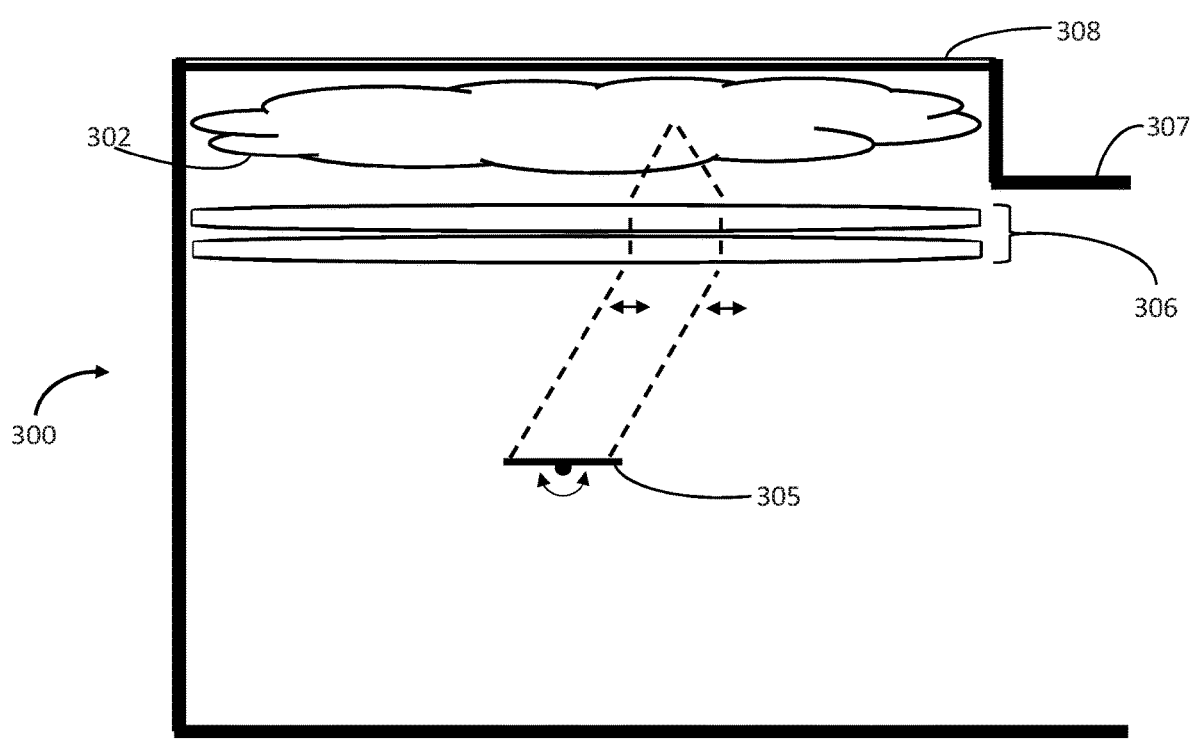
Figure 3C:
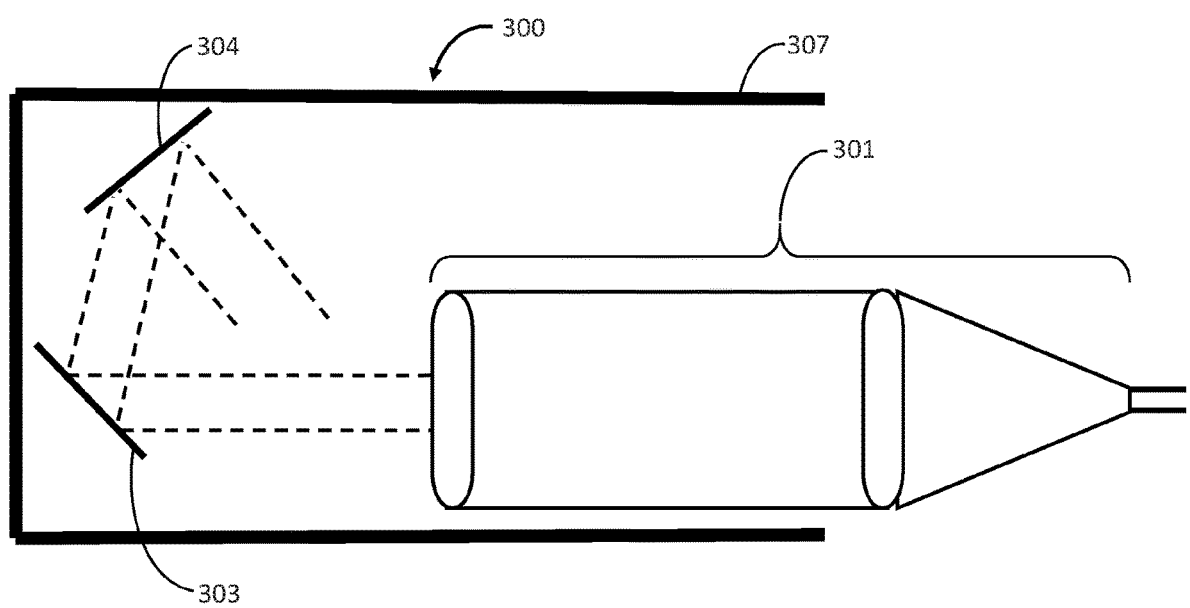

FIG. 3A, FIG. 3B, and FIG. 3C are diagrams showing an apparatus for imaging a core biopsy specimen after removal from a patient and before removal from the core biopsy device.

FIG. 4A, FIG. 4B, FIG. 4C, and FIG. 4D are diagrams showing an apparatus for containing and positioning core biopsy specimens 401 after removal from a patient in a configuration amenable to OCT imaging, according to an embodiment.

Figure 5:
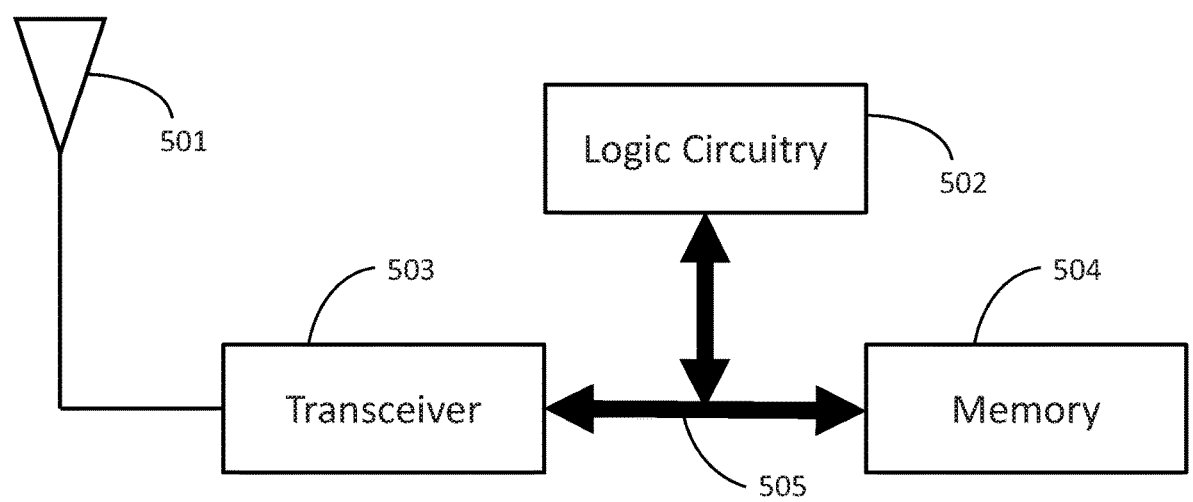

FIG. 5 is a block diagram of a hardware device that may be used to carry out one or more of the methods or processes described herein.

DESCRIPTION

The term "image" as used herein shall refer to any multidimensional representation, whether in tangible or otherwise perceptible form, or otherwise, whereby a value of some characteristic (amplitude, phase, etc.) is associated with each of a plurality of locations corresponding to dimensional coordinates of an object in physical space, though not necessarily mapped one-to-one thereonto. Thus, for example, the graphic display of the spatial distribution of some field, either scalar or vectorial, such as brightness or color, constitutes an image. So, also, does an array of numbers, such as a 3D holographic dataset, in a computer memory or holographic medium. Similarly, "imaging" refers to the rendering of a stated physical characteristic in terms of one or more images.

The term "specimen" as used herein shall refer to a tangible, non-transitory physical object capable of being rendered as an image.

Core needle biopsy procedures described herein may include vacuum-assisted needle biopsy procedures or any other tissue specimens acquired with a needle or similar device. The resulting tissue specimens are alternatively referred to as "cores," "core specimens," "core biopsy specimens," or "core needle specimens."

According to an embodiment, a core biopsy needle is inserted into the breast of a patient and a specimen is acquired through the needle channel, the specimen being pulled by a vacuum into a cylindrical specimen holder having multiple slots for specimen storage and a reference reflective surface located on the outermost extent of the cylindrical specimen holder. Each specimen slot is numbered so that information on a specific specimen may be tracked and reported.

In an embodiment, after specimen entry into the holder, a 3D optical coherence tomography data set is acquired from the entire specimen (i.e., such that data from all relevant tissue structures are captured). The image data are acquired using imaging optics located centrally to the specimen holder, with the imaging beam extending radially outward from the optics toward the reference surface. The image data are fed to a graphical processing unit-based interferometric synthetic aperture microscopy (ISAM) process (e.g., carried out by software executed by logic circuitry) to improve out-of-focus image resolution.

According to an embodiment, the 3D ISAM image data, and optionally patient history and previously-acquired mammography data, are then processed locally or sent to cloud-based remote processing hardware that carries out a classification process. The processing hardware may include one or more computer processors or graphical processing units and may have the architecture described in conjunction with FIG. 5.

In an embodiment, the classification process (i.e., the processing hardware executing software) measures the refractive index and attenuation of the core biopsy specimens by determining the apparent distance and intensity of the reference surface, respectively. Optionally, the classification process can also assess the spectral response of the sample. The classification process uses learned characteristics from historical specimen pathology diagnoses and their corresponding 3D ISAM image data, patient history data, mammography data, refractive index data, and/or attenuation data to determine the likelihood that the specimen contains malignant tissue and the likelihood that the specimen contains adequate tissue for a subsequent pathology diagnosis. An alternative approach includes parametric analysis and classification (e.g., by the processing hardware).

According to an embodiment, the classification process (e.g., the processing hardware) reports the findings to a biopsy needle controller (i.e., logic circuitry integrated with or in communication with the biopsy needle). If the specimen is found to contain insufficient tissue for a subsequent pathology diagnosis, the needle will rotate and acquire an additional specimen in an effort to locate more appropriate tissue. If the initial specimen contained adequate tissue for a subsequent pathology diagnosis, the needle will acquire additional specimens from the same location in an effort to completely remove all accessible malignant tissue. After each tissue removal, data will be sent to the cloud computing hardware and the classification process will update, returning feedback to the biopsy needle controller.

In an embodiment, upon completion of the tissue removal process, the classification process will automatically issue a final report, including a malignancy likelihood score, an imaging disposition score, similar to a BIRADS score, and pathology guidance. The pathology guidance includes information on the most important specimens to target for histology analysis and those specimens that would benefit from immunohistochemical analysis.

In an embodiment, histology analysis is performed on the numbered specimens, the results of which, when linked to the corresponding OCT imaging and other classification algorithm input data, are used as data for improvement of the classification algorithm. In an embodiment, the classification algorithm incorporates one or both of an artificial intelligence algorithm and a machine learning algorithm. In the case of an artificial intelligence or machine learning algorithm, these data form a feedback loop for continuous learning.

Alternatively to the specimen holder described, the specimens may enter a tray or basket external to the biopsy device. In this case, OCT image acquisition would be performed outside the biopsy needle device where the tray may be moved to an imaging device, (e.g., as a slide is place onto a microscope) or samples may be placed directly into an imaging device. As will be discussed below in further detail, FIG. 4A, FIG. 4B, FIG. 4C, and FIG. 4D show a hardware device configured to accept such specimens samples.

Figure 1:
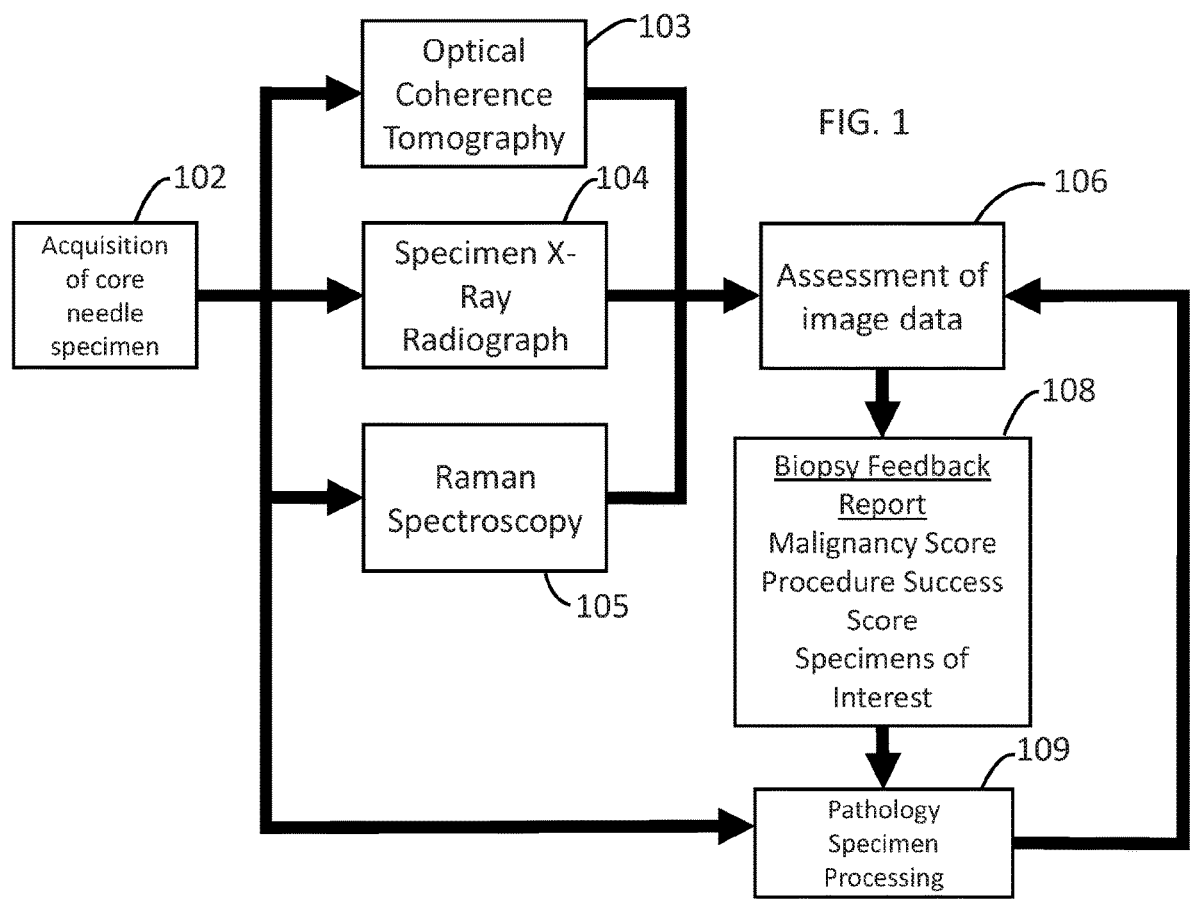
FIG. 1 is a block diagram showing a method for classification of core biopsy specimens, according to an embodiment.

Turning to FIG. 1, a method for classifying core biopsy specimens, according to an embodiment, will now be described. The acquisition of a core needle specimen is carried out (e.g., via a needle device having an integrated numbered specimen holder) at block 102. The core specimens are transferred to imaging devices in the specimen capture tray and image data are acquired from each specimen with optical coherence tomography at block 103, x-ray radiography at block 104, and Raman spectroscopy at block 105. An assessment of the image data and data from the patient's medical record, such as pre-biopsy image data (e.g., x-ray mammography, MRI, or ultrasound), is performed via an assessment algorithm at block 106 (e.g., a process carried out by logic circuitry operating according to computer executable instructions that include an image classification algorithm), resulting in the generation of a biopsy feedback report at block 108. The biopsy feedback report includes data on adequacy of the specimens obtained, the likelihood that they contain a malignancy, the regions and/or specimens most likely to contain diagnostic tissue, and the approximate dimensions, area, and volume of abnormal tissue. The specimens undergo conventional post-procedure pathology specimen processing at block 109, which yields data on the microscopic specimen properties that are input into the assessment algorithm from block 106 for training and improvement of future specimen assessments.

Figure 2A:
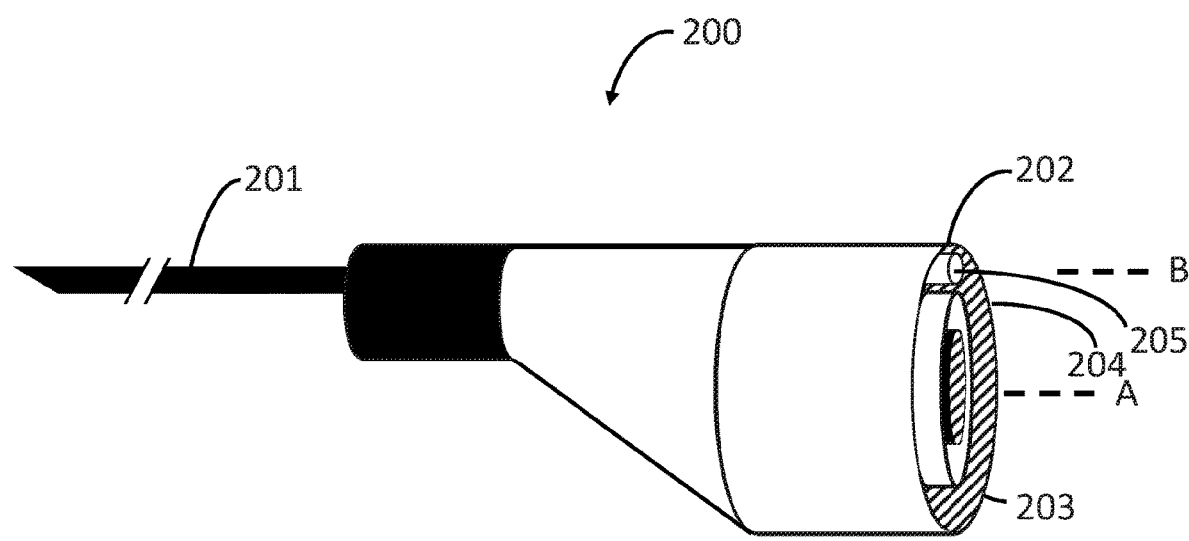
FIG. 2A is a side view of an embodiment of an apparatus for the acquisition and classification of core biopsy specimens.
Figure 2B:
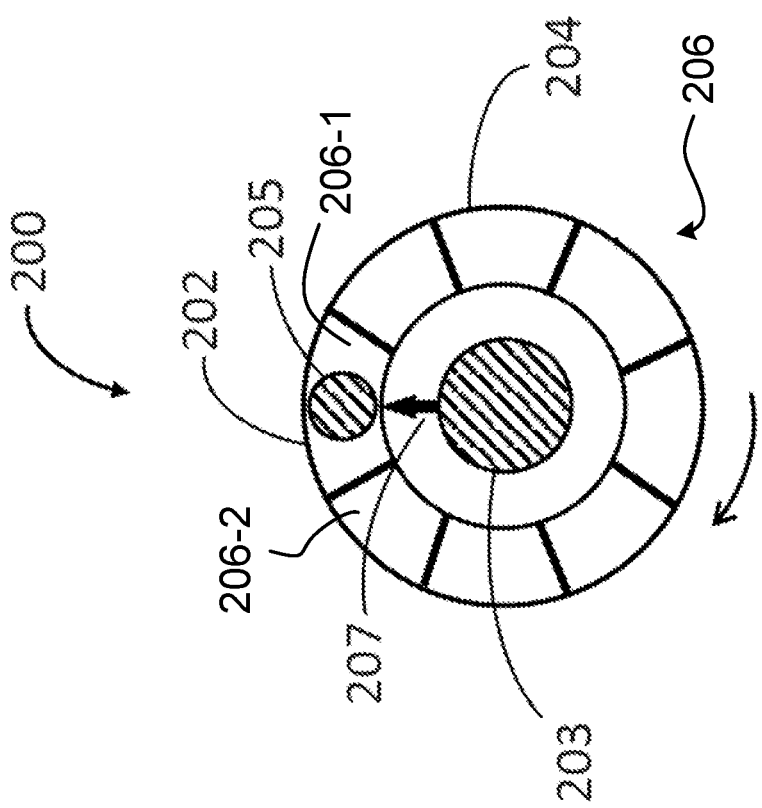
FIG. 2B is an end view of the apparatus of FIG. 2A.
Figure 2C:
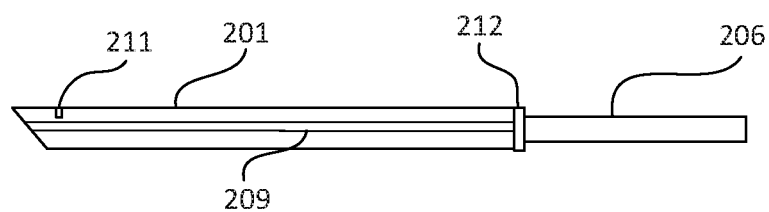
FIG. 2C is a partial diagram of the inside of the apparatus of FIGS. 2A and 2B.

Turning to FIG. 2A, FIG. 2B, and FIG. 2C an apparatus for the acquisition and classification of core biopsy specimens will now be described. The apparatus, generally labeled 200, may be used as the needle device in the method described in conjunction with FIG. 1. The apparatus 200 incorporates a core needle 201, which acquires the specimen (in a hollow portion 210 of the core needle 201), and a specimen holder 204 having multiple chambers or segments 206, including at least a first chamber or segment 206-1 and a second chamber or segment 206-2. During use, the core needle 201 gets inserted into tissue so that a hollow portion 210 of the core needle 201 is adjacent to the tissue being removed. The apparatus includes a cutting tool 211 that cuts a core of tissue from the rest of the tissue (which is now the specimen) and a vacuum device 212 that uses negative pressure to pull the specimen into a segment 206 (e.g., the first segment 206-1) that is adjacent to the core needle. The interior of the segment 206 and the hollow portion 210 are in communication via a passageway or hole. A core biopsy specimen 205 is shown in the first segment 206-1 of the specimen holder 204 after acquisition from the patient. Because the specimen holder 204 is divided into segments 206, the apparatus 200 allows for the acquisition of multiple core specimens via rotation of the specimen holder 204 so that an empty segment (e.g., the second segment 206-2) can move into a position that is adjacent to (e.g., aligned with) the core needle, thereby replacing a segment that already contains a specimen (e.g., the specimen holder is movable to align one of the plurality of segments with the core needle at a time). For example, such movement could mean rotating the specimen holder about an axis (axis A in FIG. 2A) that is parallel to a longitudinal axis (axis B in FIG. 2A) of the core needle. In some embodiments, it is the needle that rotates into position adjacent to the empty segment. Optical coherence tomography imaging (e.g., block 103 of FIG. 1) is performed by a centrally-located optical system 203, which interrogates an outwardly-located specimen (e.g., the specimen 205) via a radially-oriented optical beam 207 (FIG. 2B). The specimen holder 204 incorporates a reflective outer surface 202 that serves as a reference for the measurement of the specimen refractive index and attenuation.

Turning to FIG. 3A, FIG. 3B, and FIG. 3C, an apparatus for imaging a core biopsy specimen after removal from a patient and before removal from the core biopsy device according to an embodiment will now be described. The apparatus, generally labeled 300, includes sample-arm OCT optics configured for scanning a focused beam across a specimen and is compatible with the apparatus 200 shown in FIG. 2A and FIG. 2B (i.e., the optics in FIG. 3A, FIG. 3B, and FIG. 3C may be used as the optical system 203). The axial view shown in FIG. 3A shows an optical path (dashed line, partially obscured by collimator 301) of light extending from a collimator 301 to a specimen 302 and reflecting off of a fixed mirror 303 (dotted line indicates its location behind the collimator 301, beam steering is indicated by arrows), a fixed mirror 304, and a scanning mirror 305 (partially dotted line indicates its location partially behind collimator 301). The mirrors focus the light into specimen 302 via a set of telecentric focusing optics 306. A specimen holder 307 integrates a reflective surface 308 (or other form of optical property measurement assembly) to facilitate measurement of optical attenuation and refractive index from the specimen 302.

FIG. 3B shows a cross-sectional side view of the apparatus 300 in the plane containing specimen 302. In this view, the elongated nature of specimen 302 is visible and the movement and beam steering function of the scanning mirror 305 is indicated by the arrows. FIG. 3C shows a cross-sectional side view of the apparatus in the plane containing the collimator 301. In this view, the physical configuration of the collimator 301, the fixed mirror 303, and the fixed mirror 304 is shown.

Figure 4A:
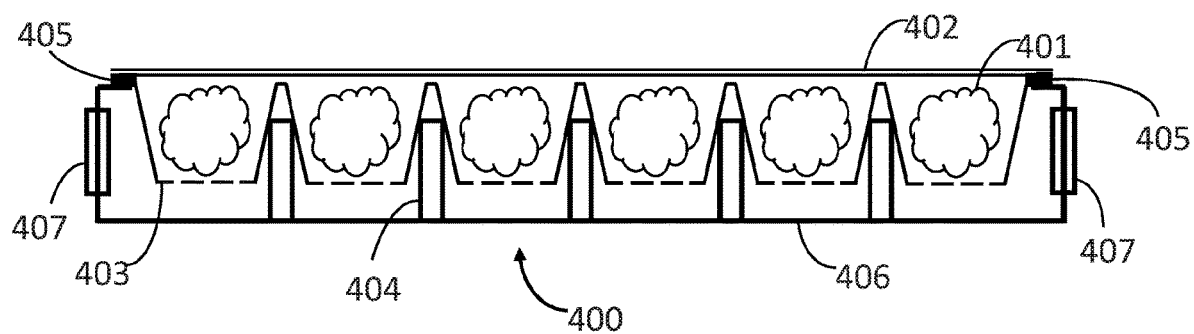

FIG. 4A, FIG. 4B, FIG. 4C, and FIG. 4D are diagrams showing an apparatus, generally labeled 400, for containing and positioning core biopsy specimens 401 after removal from a patient in a configuration amenable to OCT imaging. FIG. 4A is a cross-sectional front view of the apparatus 400 showing a clear optical cover glass 402 on top through which the focused OCT sample arm beam passes. The cover glass 402 may optionally incorporate an anti-reflective coating to facilitate transmission of the OCT sample arm beam. The specimens 401 are held in a removable tray 403 that is inserted in the apparatus 400 and held in place by a set of guide posts 404 on the bottom and a lip and gasket 405 on the top. The gasket 405 also serves to seal the apparatus 400. The bottom of the apparatus 400 forms a reservoir 406 that can be filled with a liquid (e.g., saline or formalin) via ports 407 to hydrate or preserve the specimens 401 as needed. The ports 407 can be opened and closed with a removable silicone cap (not pictured). Note that the tray 403 has holes at the bottom (shown as a dashed line) to allow a liquid to surround the specimens 401.

Figure 4B:
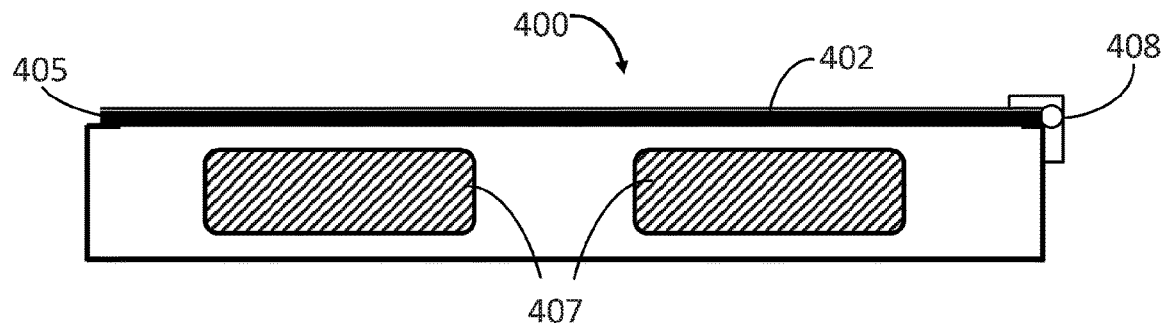
Figure 4C:
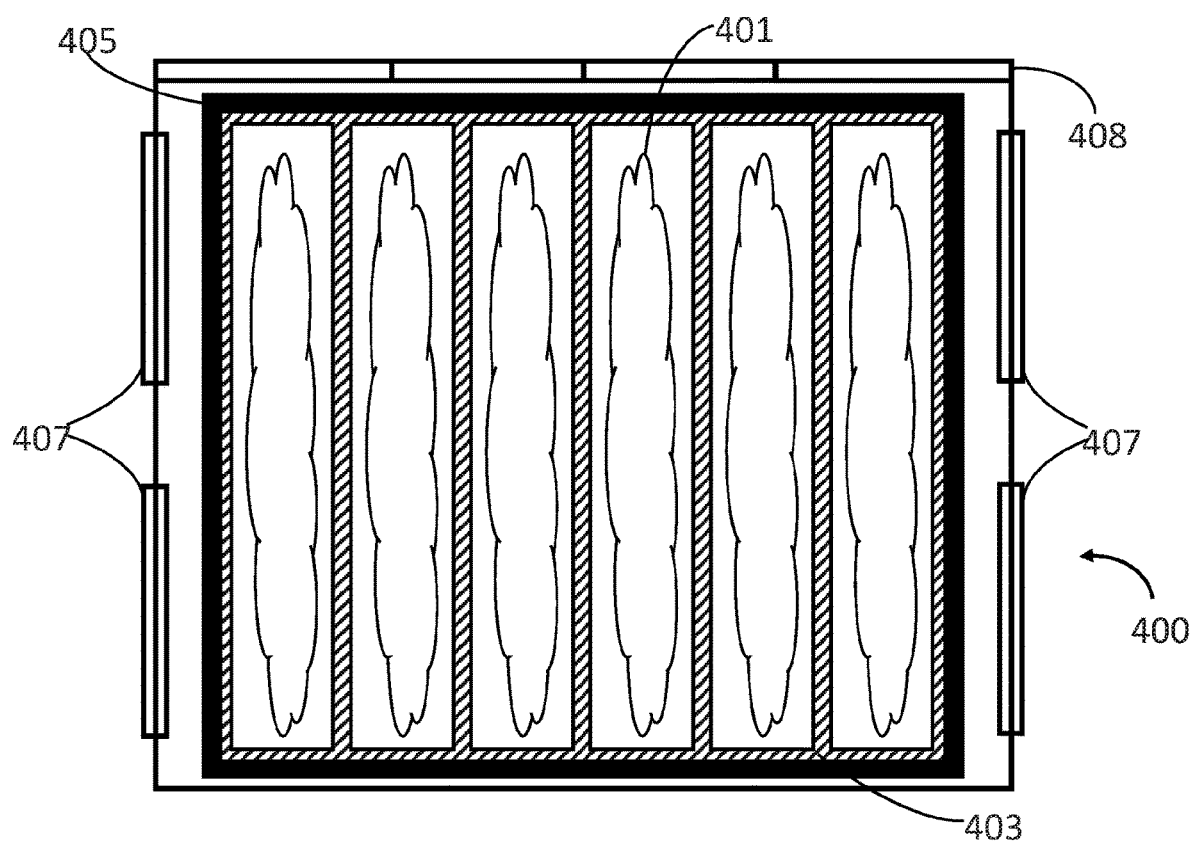
Figure 4D:
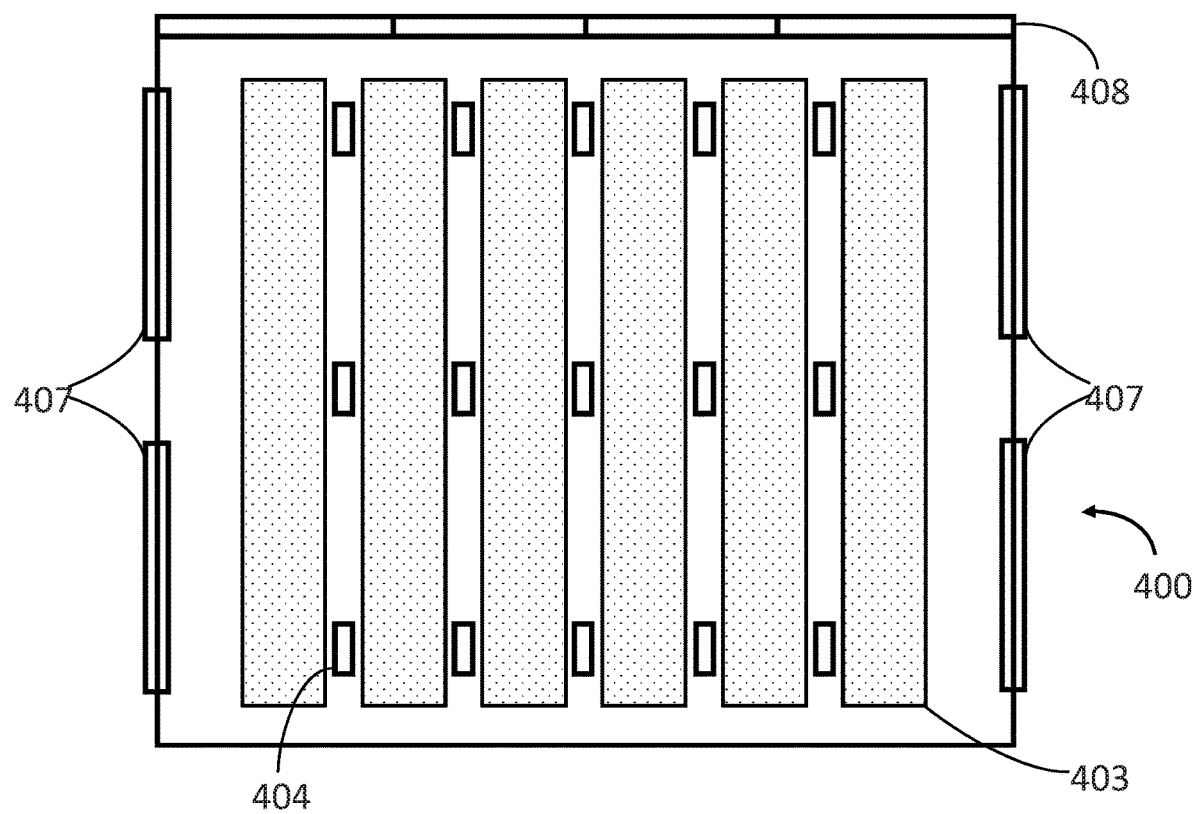

FIG. 4B is a side view showing the configuration of the ports 407, cover glass 402, and gasket 405. It further shows a hinge 408 that allows opening and closing of the lid for insertion and removal of the tray 403. FIG. 4C is a top view of the apparatus 400, showing the elongated nature of the specimens 401, their placement in the tray 403 (shown shaded), and the locations of the ports 407 and the hinge 408. FIG. 4D is a bottom view of the apparatus showing the bottom of tray 403 (with holes indicated by dotted texture) and the location of guide posts 404. Note that the apparatus physically constrains the vertical movement of specimens 401 so that they are positioned in a fixed location relative to the OCT sample arm focusing optics located above the apparatus (not pictured).

FIG. 5 illustrates a basic hardware architecture implemented by each of the one or more of the computing devices depicted in FIG. 1, according to an embodiment. The elements of FIG. 1 may have other components as well. The hardware architecture depicted in FIG. 5 includes logic circuitry 502, a memory 504, a transceiver 503, and, optionally, one or more antennas represented by an antenna 501

(including transmit antennas and/or receive antennas). The device of FIG. 5 may be communicatively linked to any of the devices depicted in FIG. 1 and FIG. 2 by, for example, one or more wired links and/or one or more wireless links. Each of the elements of FIG. 5 are communicatively linked to one another via one or more data pathways 505. Examples of data pathways include wires, conductive pathways on a microchip, and wireless connections.

Example implementations of the memory 504 include a non-transitory computer-readable medium (such as solid-state memory or magnetic storage memory). The logic circuitry 502 is a circuit (a type of electronic hardware) designed to perform complex functions defined in terms of mathematical logic. Example implementations of the logic circuitry 502 include a microprocessor, a graphics processing unit, a field-programmable gate array, a controller, or an application-specific integrated circuit.

The embodiments described above are intended to be merely exemplary; numerous variations and modifications will be apparent to those skilled in the art. All such variations and modifications are intended to be within the scope of these descriptions.

We claim:

1. A method for classifying core biopsy specimens, the method comprising:

obtaining a core biopsy specimen with a core needle;

transferring the core biopsy specimen to a specimen holder coupled to the core needle, wherein the specimen holder comprises a plurality of segments and transferring the core biopsy specimen to the specimen holder comprises transferring the core biopsy specimen to a first segment of the plurality of segments, and wherein the first segment is located adjacent to the core needle;

acquiring image data from the core biopsy specimen with an optical coherence tomography system coupled to the specimen holder;

applying a tissue classification process to the acquired image data;

providing feedback to a user based on the tissue classification process;

acquiring one or more of patient demographic data, clinical data, and prior imaging data from patient records;

assessing the acquired data in combination with the acquired optical coherence tomography image data from the core biopsy specimen;

moving the specimen holder so that the first segment is no longer adjacent to the core needle and a second segment of the plurality of segments is adjacent to the core needle;

obtaining a second core biopsy specimen with the core needle;

transferring the second core biopsy specimen to the second segment; and repeating the acquiring, applying, and providing steps for the second core biopsy specimen.

2. The method of claim 1, wherein moving the specimen holder so that the first segment is no longer adjacent to the core needle and a second segment of the plurality of segments is adjacent to the core needle comprises rotating the specimen holder about an axis that is parallel to a longitudinal axis of the core needle.

3. The method of claim 1, further comprising using an output from the tissue classification process to spatially direct the acquisition of additional biopsy specimens.

* * * * *